(12) United States Patent
Morris et al.

(10) Patent No.: US 7,993,355 B2
(45) Date of Patent: *Aug. 9, 2011

(54) METHOD AND DEVICE FOR SUTURE ISOLATION

(76) Inventors: John K. Morris, Ann Arbor, MI (US); Robert A. Van Wyk, Largo, FL (US)

( * ) Notice: Subject to any disclaimer, the term of this patent is extended or adjusted under 35 U.S.C. 154(b) by 1509 days.

This patent is subject to a terminal disclaimer.

(21) Appl. No.: 11/386,860

(22) Filed: Mar. 22, 2006

(65) Prior Publication Data

US 2006/0167479 A1   Jul. 27, 2006

Related U.S. Application Data

(63) Continuation-in-part of application No. 10/875,766, filed on Jun. 24, 2004, now Pat. No. 7,704,263.

(60) Provisional application No. 60/484,243, filed on Jul. 2, 2003.

(51) Int. Cl.
A61B 17/10 (2006.01)
A61B 17/04 (2006.01)

(52) U.S. Cl. .......................... 606/148; 606/139; 606/145

(58) Field of Classification Search ............. 289/13–15; 600/206, 208, 233; 606/139, 145, 148
See application file for complete search history.

(56) References Cited

U.S. PATENT DOCUMENTS

| | | | |
|---|---|---|---|
| 4,185,636 A | 1/1980 | Gabbay et al. | 128/334 |
| 4,586,614 A | 5/1986 | Ger | 211/41 |
| 5,041,095 A * | 8/1991 | Littrell | 604/167.04 |
| 5,207,703 A | 5/1993 | Jain | 606/232 |
| 5,282,533 A | 2/1994 | Holzwarth et al. | 206/63.3 |
| 5,335,775 A | 8/1994 | Scanlon et al. | 206/63.3 |
| 5,437,646 A * | 8/1995 | Hunt et al. | 604/167.04 |
| 5,538,132 A | 7/1996 | Propp et al. | 206/365 |
| 5,728,151 A | 3/1998 | Garrison et al. | 623/2 |
| 5,951,467 A * | 9/1999 | Picha et al. | 600/233 |
| 5,972,030 A * | 10/1999 | Garrison et al. | 623/2.11 |
| 6,010,531 A | 1/2000 | Donlon et al. | 623/2 |
| 6,045,573 A | 4/2000 | Wenstrom, Jr. et al. | 606/232 |
| 6,190,396 B1 | 2/2001 | Whitin et al. | 606/144 |
| 6,280,460 B1 | 8/2001 | Bolduc et al. | 606/222 |
| 6,416,469 B1 | 7/2002 | Phung et al. | 600/232 |
| 6,450,951 B2 | 9/2002 | Phung et al. | 600/215 |
| 6,451,054 B1 | 9/2002 | Stevens | 623/2.11 |
| 6,564,805 B2 | 5/2003 | Garrison et al. | 128/898 |
| 6,599,240 B2 | 7/2003 | Puchovsky et al. | 600/232 |
| 6,651,671 B1 | 11/2003 | Donlon et al. | 128/898 |
| 6,709,441 B2 | 3/2004 | Bolduc et al. | 606/153 |
| 2003/0187466 A1 | 10/2003 | Snyder | 606/148 |
| 2004/0073233 A1 | 4/2004 | Jannot | 606/148 |
| 2005/0065535 A1 * | 3/2005 | Morris et al. | 606/148 |

* cited by examiner

*Primary Examiner* — Darwin P Erezo
*Assistant Examiner* — Melissa Ryckman
(74) *Attorney, Agent, or Firm* — Chalin A. Smith; Smith Patent Consulting

(57) ABSTRACT

A method and device provides features for the temporary "parking" of sutures with respect to a cannula. In the preferred embodiments the features are slots that maintain tension on, and orientation of, sutures placed therein. The slots or features may be integral with the cannula or part of a separate device which may be removably affixed to the external portion of a cannula. In addition, the opening(s) used for instrument-passing are off-center, thereby reducing if not eliminating outward sprays during use. The invention eliminates the multiple steps inherent in current suture management techniques for arthroscopic procedures, particularly rotator cuff repair and assists in tensioning/advancement of tissue into its repair site.

17 Claims, 22 Drawing Sheets

SECTION A-A

SECTION B-B

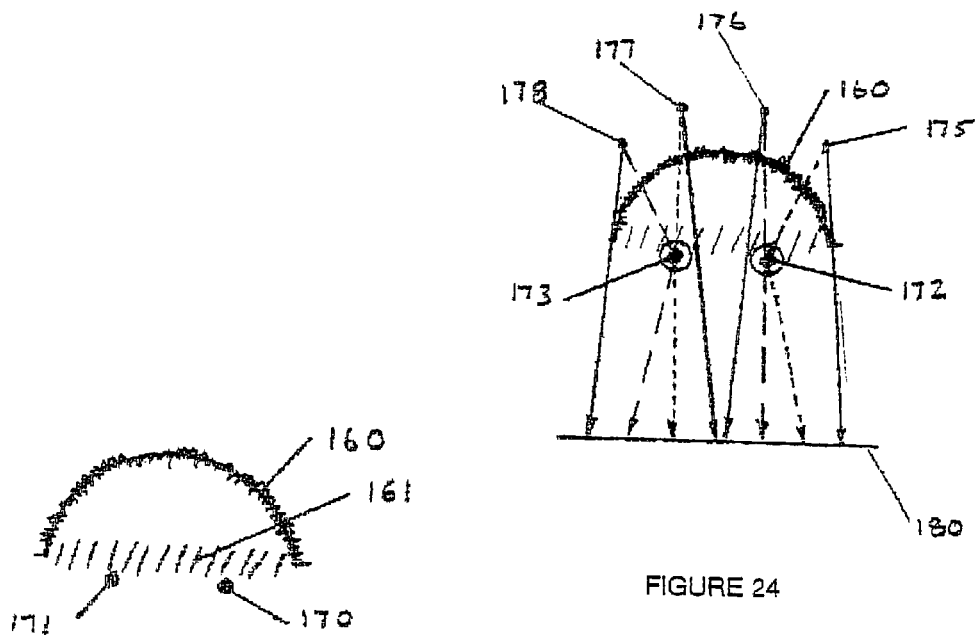
FIGURE 24
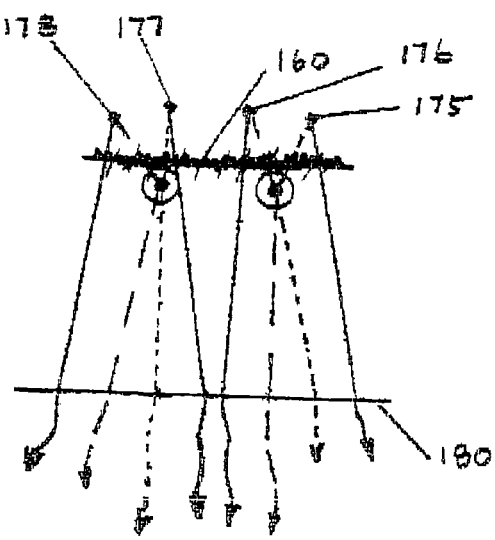
FIGURE 23
FIGURE 25

SECTION B-B

METHOD AND DEVICE FOR SUTURE ISOLATION

REFERENCE TO RELATED APPLICATIONS

This application is a continuation-in-part of U.S. patent application Ser. No. 10/875,766, filed Jun. 24, 2004 now U.S. Pat. No. 7,704,263, which claims priority from U.S. Provisional Patent Application Ser. No. 60/484,243, filed Jul. 2, 2003, the entire content of both of which are incorporated herein by reference.

FIELD OF THE INVENTION

The disclosed invention relates to arthroscopic surgery, and more particularly, to the control of sutures to prevent tangling during arthroscopic procedures including rotator cuff repair, labral repair and other soft tissue apposition.

BACKGROUND OF THE INVENTION

The advantages of arthroscopic surgery are significant, however, the procedure has been technically demanding, particularly with respect to rotator cuff repair. The introduction of second-generation anchors with improved holding power and larger eyes which allow sutures to slide easily through them, and clear cannulas which improve visualization, have made the procedure easier. Until recently, however, passing suture through the cuff has been a challenging, multi-step process beyond the skill (or patience level) of many surgeons. This is especially true for surgeons who only infrequently do rotator cuff repairs.

In 2001 in the state of New York, 9,207 cuff repairs were performed by 859 surgeons. During this time period, 90 percent of the New York doctors who performed rotator cuff repairs performed 24 or fewer cuff repairs each, an average of less than one every two weeks. The infrequency with which these doctors perform the procedure generally prevents them from developing the skills necessary to perform the procedure arthroscopically. The recent introduction to the market of instruments which are able to pass braided suture without the use of a shuttle (a device which is first passed through the cuff, and is then used to pull the suture through the cuff) has removed much of the difficulty. The ExpresSew™ by Surgical Solutions, LLC (Valencia, Calif.) is able to directly pass braided suture through a cuff. The Needle Punch™ by Arthrex Incorporated (Naples, Fla.) is able to grasp the cuff, pass braided suture through the cuff, and bring the suture out through the cannula used for access (the working cannula).

While the problem of passing a suture through a cuff arthroscopically has been largely eliminated, suture management has become critical to the technical success of the surgery. Indeed, tangled sutures can terminate an arthroscopic procedure. This problem is compounded by the fact that many anchors now are loaded with two sutures so as to create two vertical stitches which can be slightly separated so as to distribute the load over a greater area of the tendon. This improves the strength of the repair, but at the same time gives the surgeon four suture "legs" with which to deal.

Arthroscopic rotator cuff repairs are performed in a space which is filled with pressurized liquid, generally normal saline, the surgeon working through various small incisions or portals. Pressurization of the joint and leakage of liquid from the joint is controlled by cannulae which are inserted into the portals, the cannulae having seals through which instruments and sutures may be passed.

Common suture management techniques call for removal of sutures from the working cannula in order to avoid tangles. The sutures are then retrieved one at a time as needed. Some advocate making extra punctures for the sole purpose of temporarily storing sutures to avoid tangles. Others recommend retrieving one suture through the mid-glenoid working cannula, and retrieving the other limbs through the anterior superior cannula, after which the cannula is removed and reinserted leaving the sutures through the portal outside the cannula. Transporting sutures from one cannula to another or to alternative portals can occupy large blocks of time during a given operation. Also, removing and reinserting a cannula may increase trauma to local tissues. There is a need for a more efficient suture management system, minimizing the multiple extra steps inherent in the currently recommended techniques and their associated increased trauma.

Performing an arthroscopic rotator cuff repair is a multi-step process. The bone bed is prepared using a high-speed buf, adjacent to the articular surface of the humeral head. Anchors are placed in the bone bed, each anchor generally loaded with two strands of suture so that four tails are created. One leg of each suture is passed through the cuff, suitably spaced so as to distribute the load over a greater area of the tendon. One set of sutures is pulled laterally as traction sutures to retain tension and position of the cuff during suture knot tying of the second set of sutures. Traction suture tension is generally maintained by an assistant holding onto the suture legs which pass from the working cannula. The traction sutures are tied after the first set of sutures. The process of applying traction and tying suture pairs is repeated until all sutures are tied. There is currently no method for applying tension to a traction suture which does not require an assistant to hold the suture.

The use of a traction suture also frequently leads to excessive leaking and spraying from the working cannula since the suture under tension often distorts the seal through which the suture passes thereby allowing the flow of liquid.

It is, accordingly, an object of this invention to produce a method for suture management which prevents tangling of sutures and allows tensioning of a traction suture without manual assistance.

It is also an object of this invention to produce a method for tensioning a traction suture while minimizing fluid leakage from the joint.

It is also an object of this invention to produce a method for tensioning a traction suture while maintaining fluid pressure within the joint.

It is also an object of this invention to produce a method for suture management which prevents tangling of sutures but does not require transporting of sutures from the working cannula to avoid tangles.

It is also an object of this invention to produce a method for suture management which prevents tangling of sutures and thereby reduces procedure time and complexity.

It is, accordingly, an object of this invention to produce a device for suture management which prevents tangling of sutures and allows tensioning of a traction suture without manual assistance.

It is also an object of this invention to produce a device for tensioning a traction suture while minimizing fluid leakage from the joint.

It is also an object of this invention to produce a device for tensioning a traction suture while maintaining fluid pressure within the joint.

It is also an object of this invention to produce a device for suture management which prevents tangling of sutures but does not require transporting of sutures from the working cannula to avoid tangles.

It is also an object of this invention to produce a device for suture management which prevents tangling of sutures and thereby reduces procedure time and complexity.

It is yet a further object of this invention to produce a device for suture management which minimizes or prevents outward spraying during use.

SUMMARY OF THE INVENTION

These and other objects are achieved in the invention herein disclosed which is a method and device for management of sutures within the working cannula through the temporary "parking" of sutures within slots on the exterior portion of the cannula, the slots maintaining tension on, and orientation of, sutures placed therein. In one embodiment the slots are integral with the cannula. In another the slots are part of a separate device which may be removably affixed to the external portion of a cannula. In yet another embodiment the cannula with integral slots has a seal configured to minimize leakage through the seal when sutures, especially traction sutures, are used in the cannula. In still another embodiment the slots are part of a separate device which removably mounts to a cannula and also includes a means for suppressing spray which escape from the cannula seal during use.

Maintaining tension on a given suture and controlling the orientation of each suture with respect to its neighbor reduces the likelihood of tangles even when all sutures are contained within the same cannula that is being used to pass instruments (the working cannula). As each suture is inserted two tails (or legs) are created. For a rotator cuff repair involving the supraspinatus tendon, one limb is below and one on top of the tendon. As the sutures are inserted this orientation is easily recognized and can be maintained by the disclosed device with slight tension on each suture limb. The tension prevents loops of suture from forming. Therefore the insertion of additional sutures is collinear with the existing sutures and tangles do not occur. As the sutures are tied down, the knots slide smoothly as the limbs' orientations have been maintained and the limbs are not crossed.

When a suture pair is to be used as a traction suture, the legs are pulled to achieve the desired displacement of the cuff and the sutures temporarily secured to the suture isolator. The axial force on the cannula due to tension in the traction suture may cause the cannula to advance into the portal. This can be prevented by affixing a suitable clamp or spacer to the cannula proximal to the portal.

The invention herein disclosed eliminates the multiple steps inherent in current suture management techniques for rotator cuff repair. This results in decreased opportunities for errors and significant time savings for the surgeon. Because the sutures are managed within the working cannula, removal and reinsertion of cannulas for suture control with the associated increased trauma to local tissues, are avoided. Also, according to a preferred embodiment of the invention, the opening(s) used for instrument-passing are off-center, thereby reducing if not elimination outward sprays during use.

These and other objects and features of the invention will become more fully apparent when the following detailed description is read in conjunction with the accompanying figures and examples.

BRIEF DESCRIPTION OF THE DRAWINGS

FIG. 23 show a top view of the rotator cuff edge;

FIG. 24 shows anchors deployed;

FIG. 25 shows the rotator cuff edge reduced into its insertion area by tensioning sutures;

DETAILED DESCRIPTION OF THE INVENTION

Figure 2:
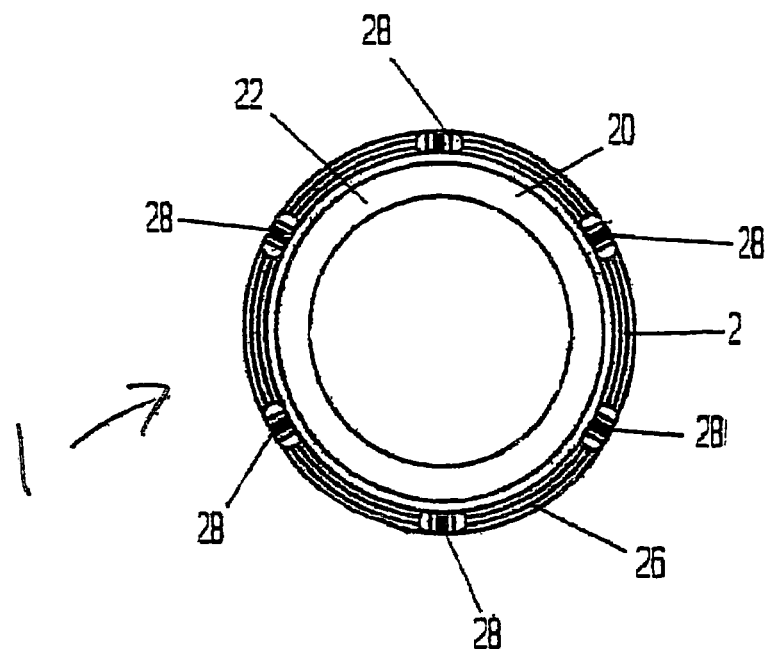
FIG. 2 is a proximal axial view of the object of FIG. 1.
Figure 1:
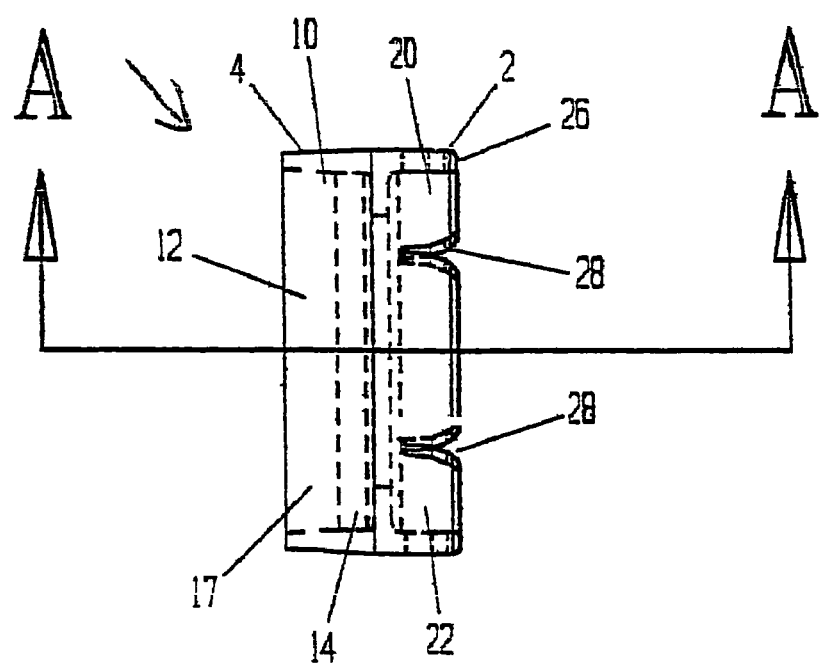
FIG. 1 is plan view of a suture isolator constructed in accordance with the principles of this invention
Figure 3:
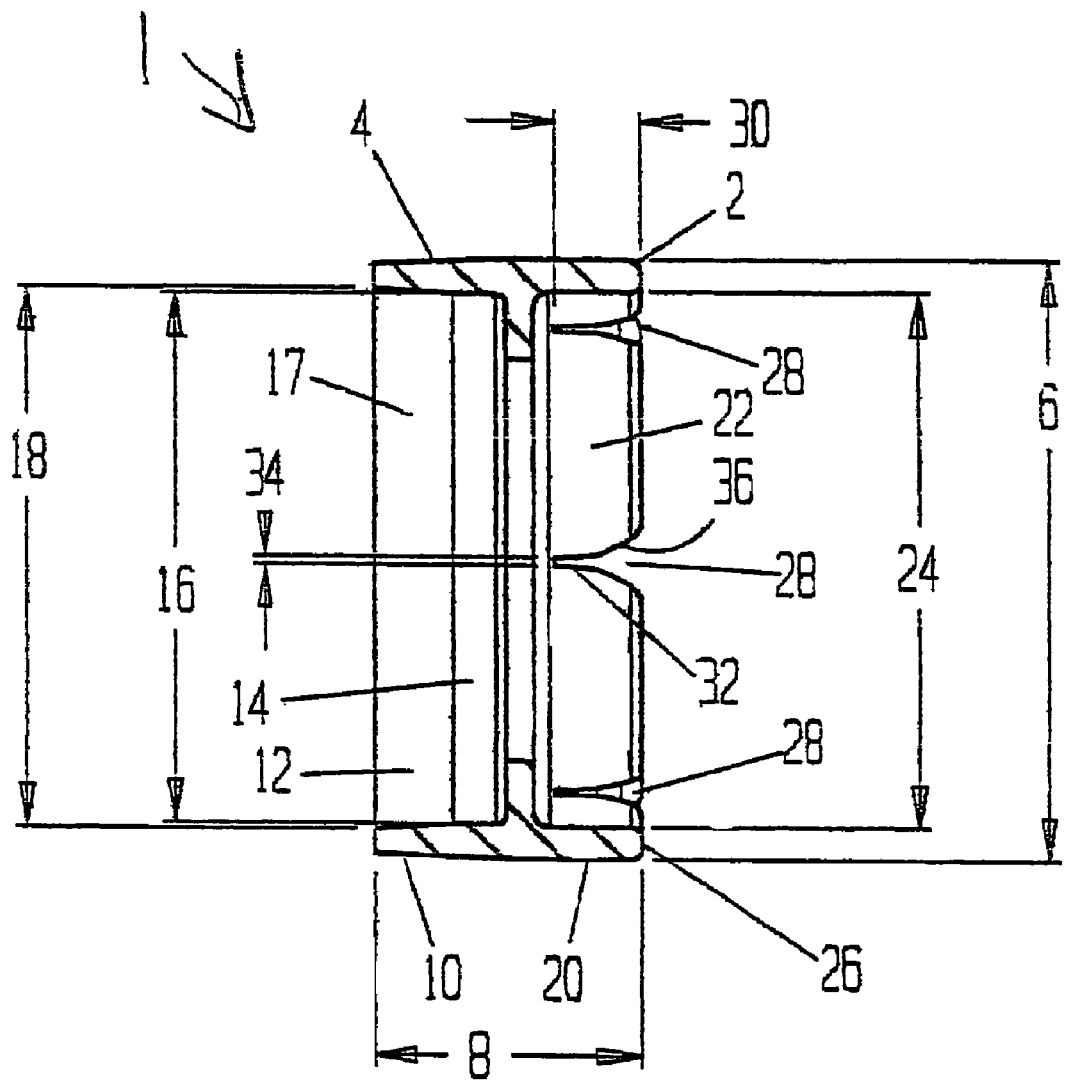
FIG. 3 is a side-elevational sectional view of the object of FIG. 1.

Referring to FIGS. 1 through 3, suture isolator 1 has a proximal end 2, a distal end 4, outer diameter 6 and length 8. Distal portion 10 has a recess 12 formed therein, recess 12 having a cylindrical portion 14 of diameter 16 and a tapered portion 17 in which the diameter increases to diameter 18. Proximal portion 20 has a cylindrical recess 22 of diameter 24 formed therein so as to produce proximal rim 26. Proximal rim 26 has a plurality of slots 28 of depth 30 having a distal portion 32 of width 34 and a tapered proximal portion 36. Width 34 of distal portion 32 is less than the thickness of the suture generally used for arthroscopic rotator cuff repair so that suture removably placed in slots 28 is held securely. Isolator 1 is made of a rigid metallic or polymeric material.

Figure 4:
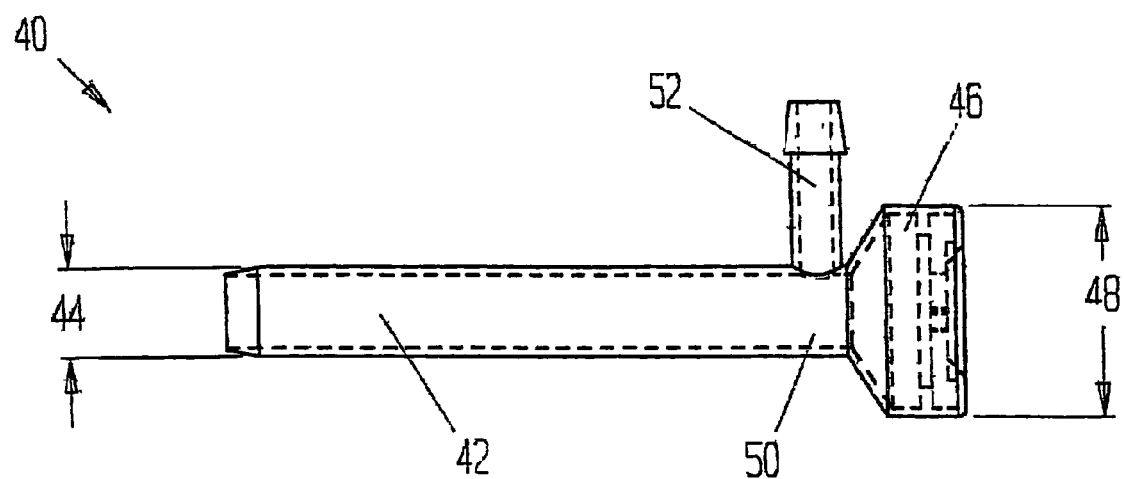
FIG. 4 is a plan view of an arthroscopy cannula of the type used with the invention herein disclosed.
Figure 5:
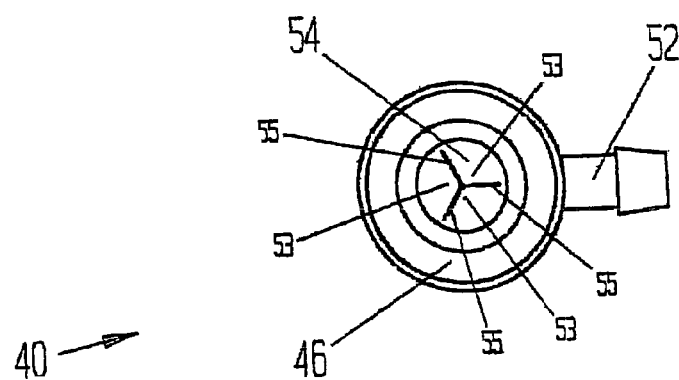
FIG. 5 is a proximal axial view of the object of FIG. 4.
Figure 6:
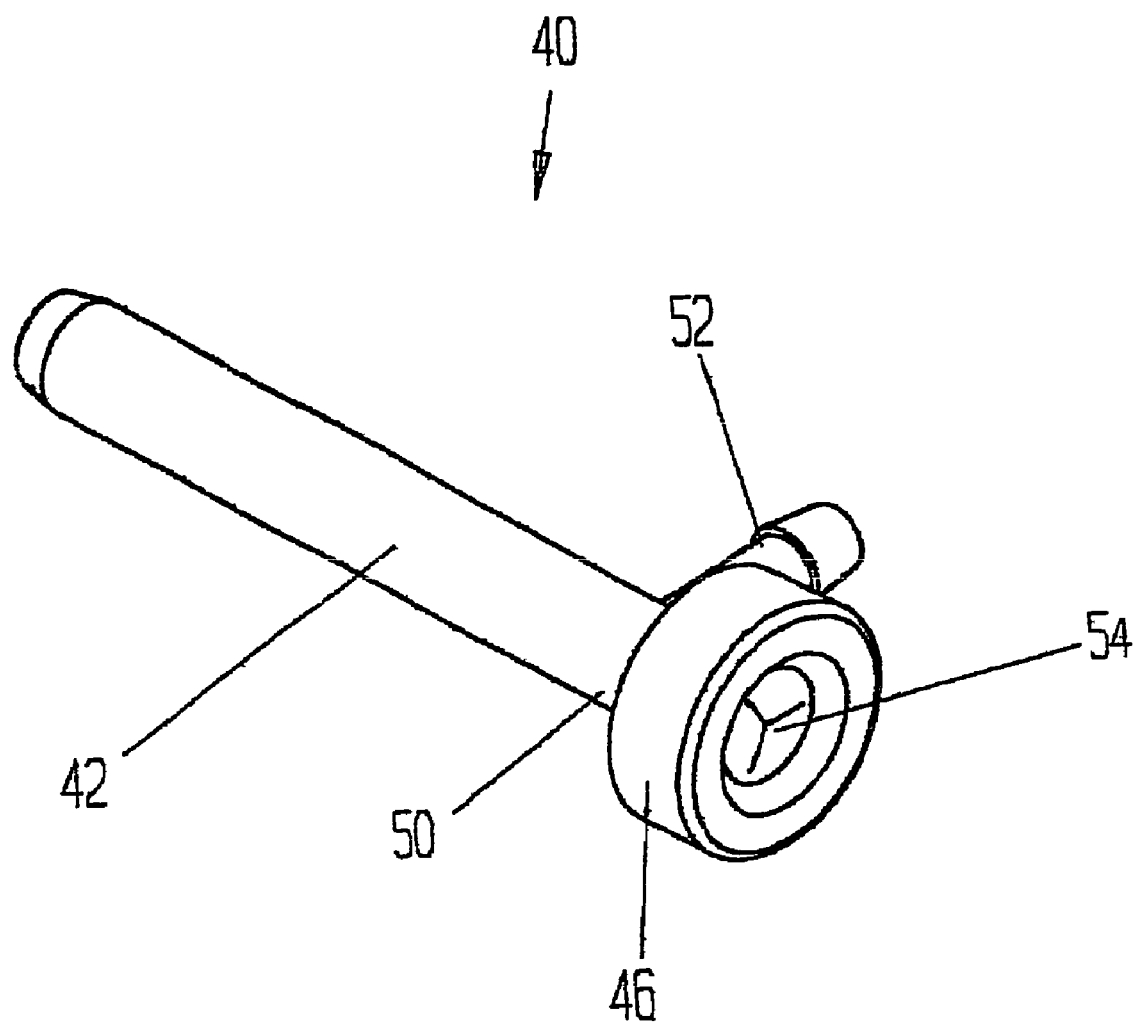
FIG. 6 is a perspective view of the object of FIG. 4.

Referring to FIGS. 4 through 6, cannula 40 has an elongated tubular distal portion 42 of diameter 44 and a proximal portion 46 of diameter 48, diameter 48 being slightly greater than diameter 16 and slightly less than diameter 18 of distal circular recess of suture isolator 1 (FIGS. 1 through 3). Near proximal end 50 of distal portion 42, inflow tube 52 provides a means for supplying irrigant to the inner lumen of distal portion 42. Deformable polymeric seal 54 having a plurality of slits 55 closely conforms to instruments placed therethrough so as minimize leakage of fluid from the site.

Figure 7:
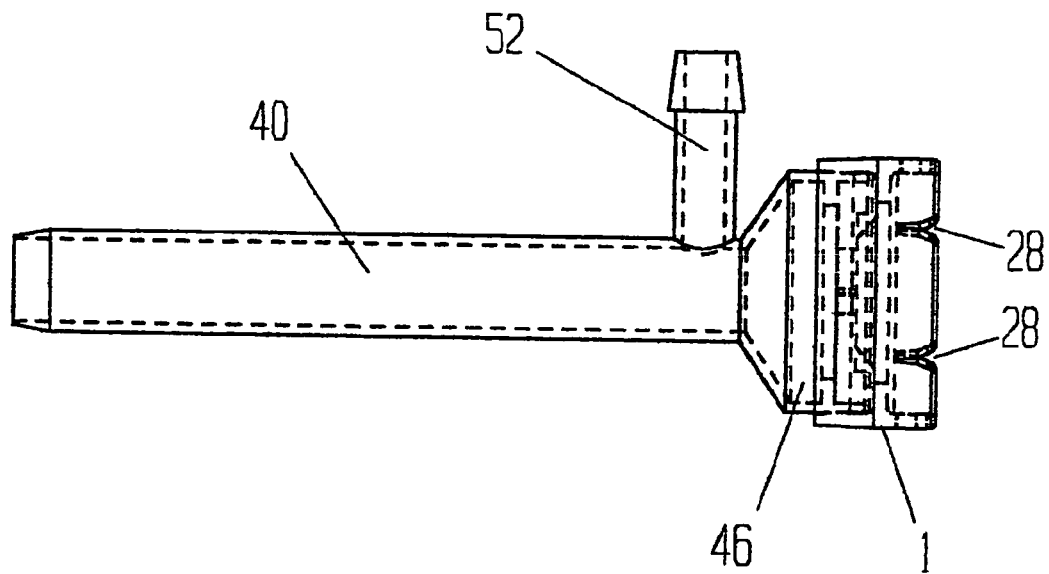
FIG. 7 a plan view of the object of FIG. 1 assembled to the object of FIG. 4.
Figure 8:
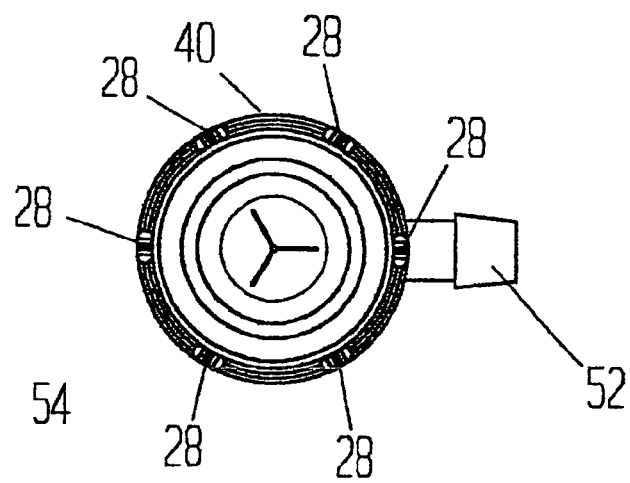
FIG. 8 is a proximal axial view of the objects of FIG. 7.
Figure 9:
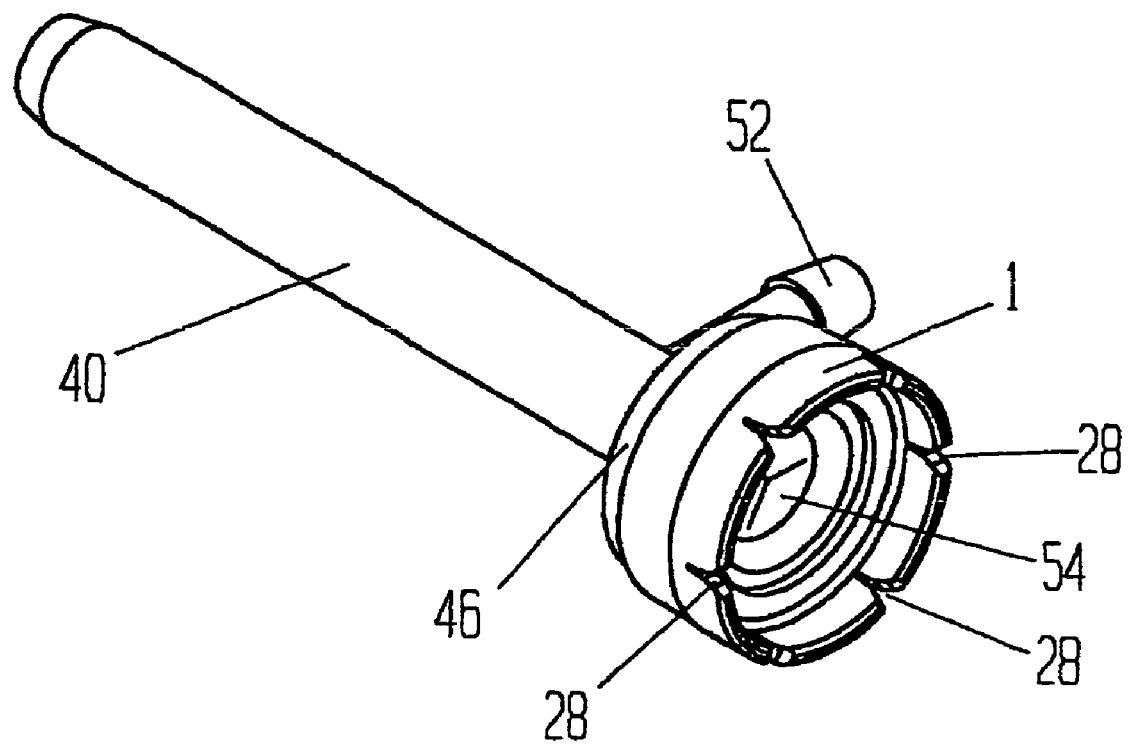
FIG. 9 is a perspective view of the objects of FIG. 7.

Referring to FIGS. 7 through 9, suture isolator 1 is removably affixed to cannula 40, cylindrical portion 14 of recess 12 of isolator 1 (FIGS. 1 through 3) deformably mating to the proximal portion of proximal portion 46 of cannula 40, diameter 48 of portion 46 being slightly larger than diameter 16 of recess 12 (FIGS. 1 through 3). Mounting of isolator 1 to cannula 40 is facilitated by tapered portion 17 of recess 12.

Figure 10:
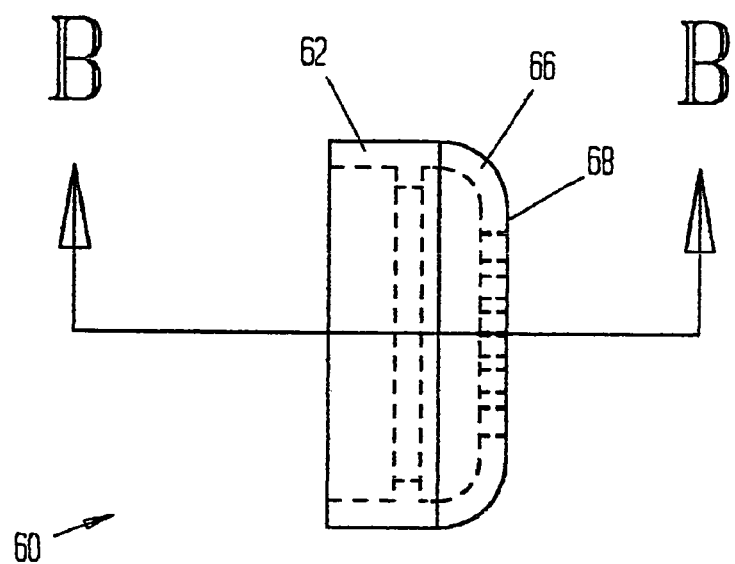
FIG. 10 is a plan view of an alternate embodiment constructed in accordance with the principles of this invention.
Figure 11:
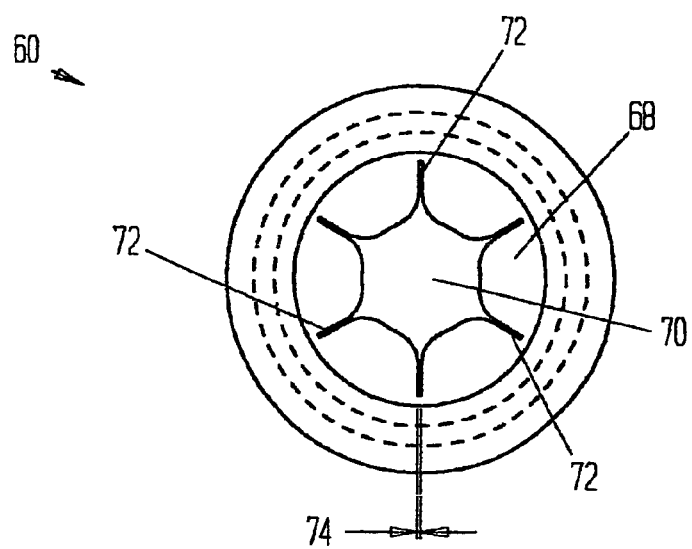
FIG. 11 is a proximal axial view of the object of FIG. 10.
Figure 12:
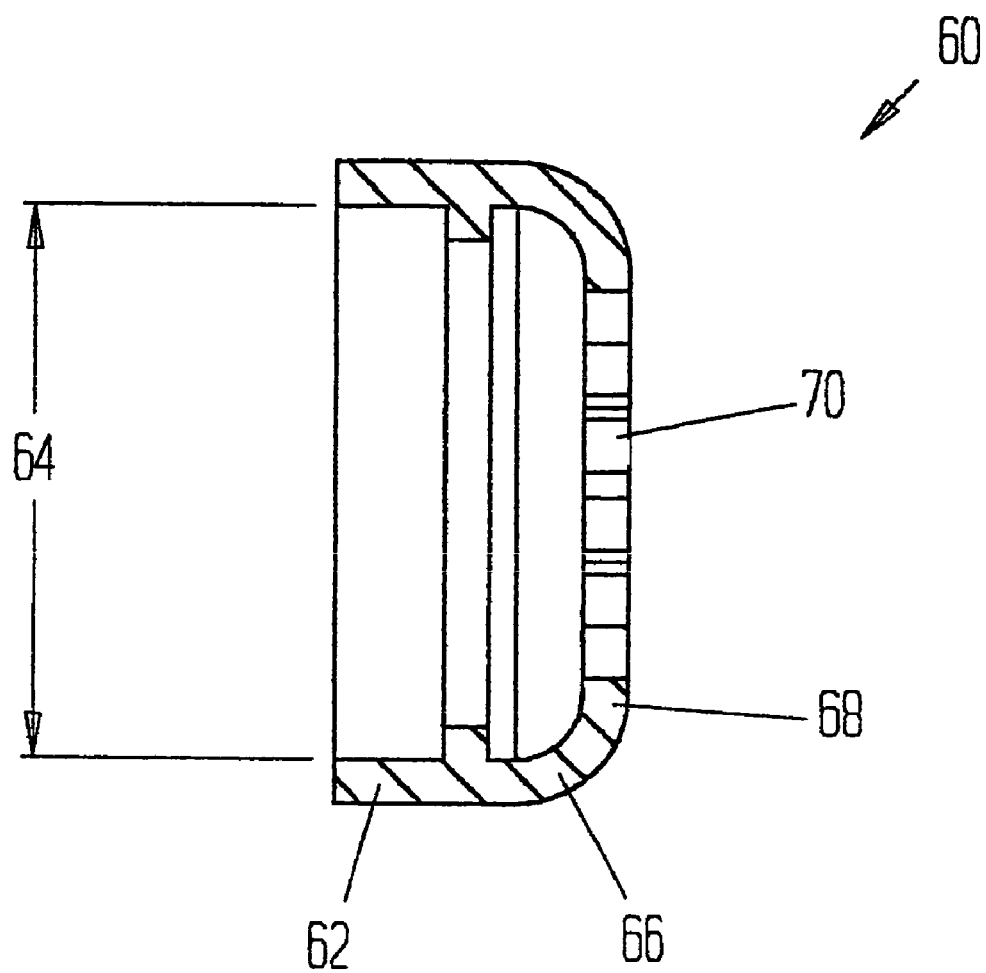
FIG. 12 is a side sectional view of the object of FIG. 10.

In another embodiment, shown in FIGS. 10 through 12, suture isolator 60, made from a suitable resilient polymeric material such as neoprene which deforms to allow the passage of instruments, has a tubular distal portion 62 having an inner cylindrical diameter 64, and a closed-end proximal portion 66 having a proximal wall 68 wherein is formed opening 70. Diameter 64 is somewhat smaller than diameter 48 of proximal portion 46 of cannula 40 (FIGS. 4 through 6). Opening 70 has a plurality of radial slots 72 having a width 74 less than the thickness of the suture generally used for arthroscopic rotator cuff repair so that suture removably placed in slots 72 is held securely.

The configuration of isolator 60 made from resilient polymeric material differs from that of isolator 1 made from rigid material. Note that whereas slots 28 of isolator 60 (FIGS. 1 through 3) are oriented axially and positioned in proximal rim 26, slots 72 are oriented radially and positioned in proximal wall 68. If an suture isolator made of a resilient material is formed like isolator 1 with radial slots in the proximal rim, stretching the isolator so that it mounts to the larger diameter of the proximal portion of a cannula may cause unacceptable widening of the slots so that suture placed therein is not securely grasped.

Figure 13:
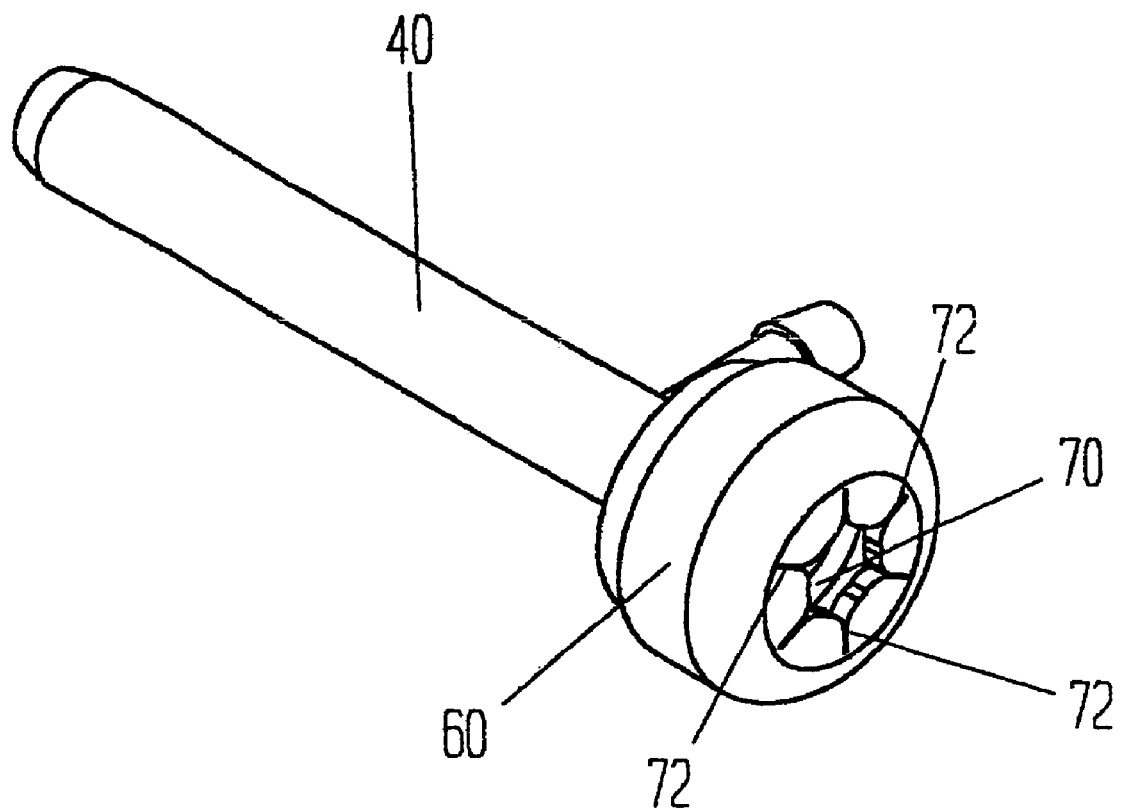
FIG. 13 is a perspective view of the object of FIG. 10 assembled to the object of FIG. 4.

Referring to FIG. 13, suture isolator 60 is removably mounted to cannula 40, distal portion 62 deformably mating to the proximal portion 46 of cannula 40, diameter 48 of portion 46 (FIGS. 7 through 9) being larger than diameter 64 of distal portion 62 of isolator 60.

Because of the resilient material of which isolator 60 is formed, the holding power of slots 72 may be insufficient for maintaining tension in some traction sutures. Accordingly, another embodiment (not shown) uses a combination of isolator 1 (FIGS. 1 through 3) and isolator 60, isolator 1 having a distal recess configured to be removably mounted to tubular distal portion 62 of isolator 60. Sutures are passed through slots 72 of isolator 60 and removably affixed to slots 28 of isolator 1, isolator 60 aiding in isolation of the sutures and preventing leakage from the seal from spraying from the isolator.

Figure 14:
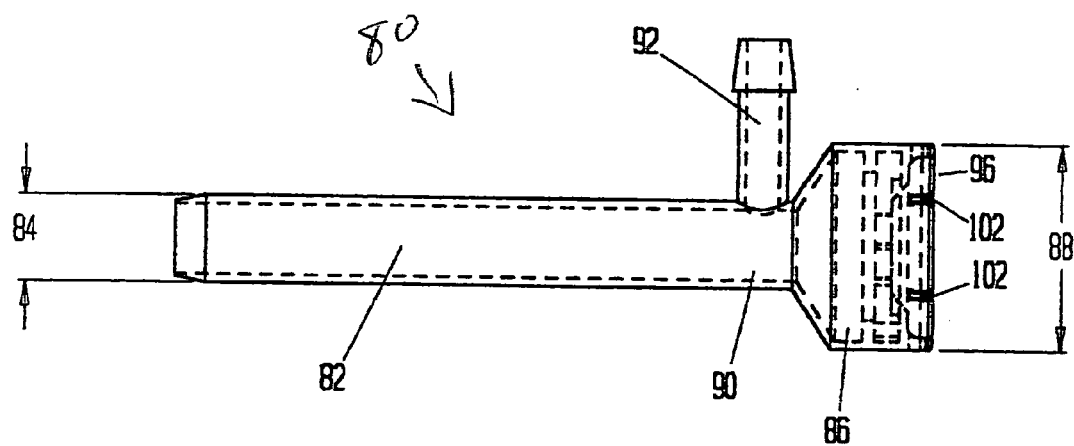
FIG. 14 is a plan view of another alternate embodiment constructed in accordance with the principles of this invention.
Figure 15:
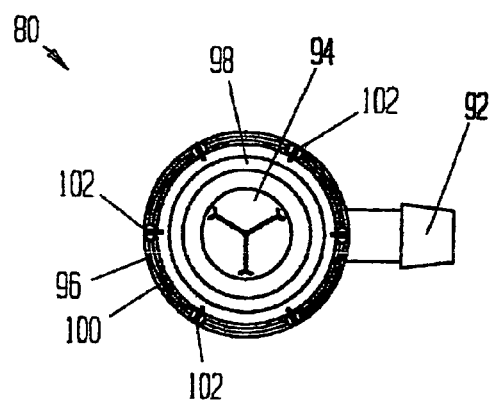
FIG. 15 is a proximal axial view of the object of FIG. 14.
Figure 16:
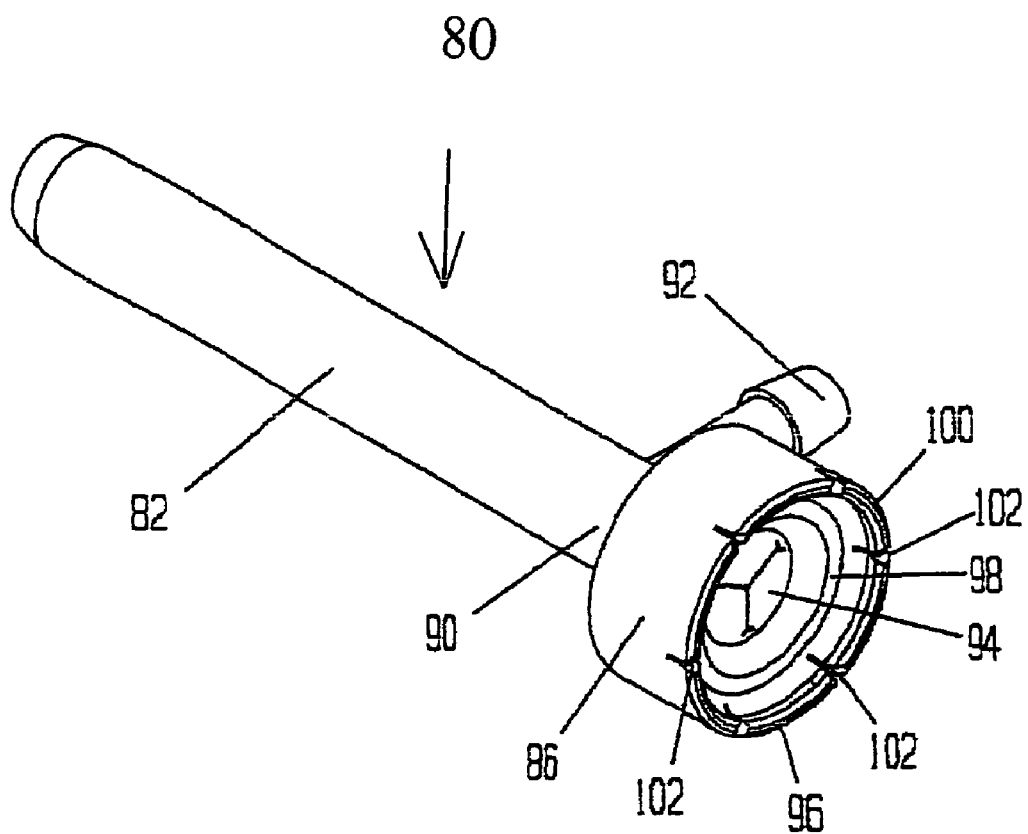
FIG. 16 is a perspective view of the object of FIG. 14.

In yet another embodiment shown in FIGS. 14 through 16, the suture retaining slots are integral to the cannula. Cannula 80 has an elongated tubular distal portion 82 of diameter 84 and a proximal portion 86 of diameter 88. Near proximal end 90 of distal portion 82, inflow tube 92 provides a means for supplying irrigant to the inner lumen of distal portion 82. Deformable polymeric seal 94 closely conforms to instruments placed therethrough so as minimize leakage of fluid from the site. Proximal-most surface 96 of proximal portion 86 has a circular recess 98 formed therein so as to form a circumferential rim 100 wherein are a plurality of slots 102, slots 102 being similar in form to slots 28 of isolator 1 (FIGS. 1 through 3). That is, slots 102 have a narrow distal portion having a width suited to releasably securing therein suture generally used for arthroscopic rotator cuff repair, and a tapered proximal portion to aid in positioning the suture within the slot.

Figure 17:
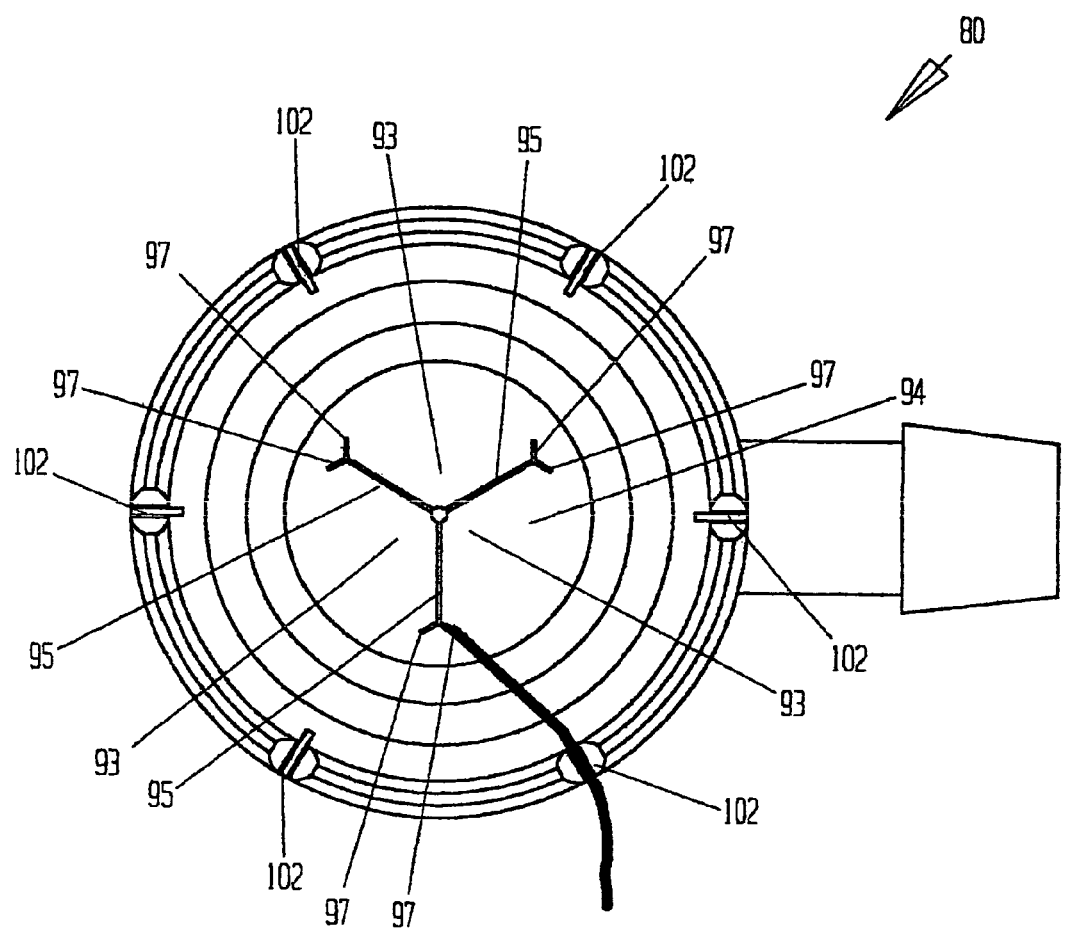
FIG. 17 is an expanded proximal axial view of the object of FIG. 14 showing suture placement in the seal during use.

Referring to FIG. 17, seal 94 has a plurality of slits 95 forming a plurality of flaps 93, slits 95 terminating in angled slits 97. During use a suture 99 which has been retrieved through cannula 80 is positioned within a slit 97 and secured in a slot 102 to maintain tension in and orientation of suture 99. When the suture has been secured, flaps 93 can return to and maintain their closed positions so as to minimize leakage through the seal. This is in contrast to seal 54 of cannula 50 (FIGS. 4 through 6) in which a suture passing through the seal and maintained under tension will frequently hold flaps 53 open thereby causing leakage through the seal.

Figure 18:
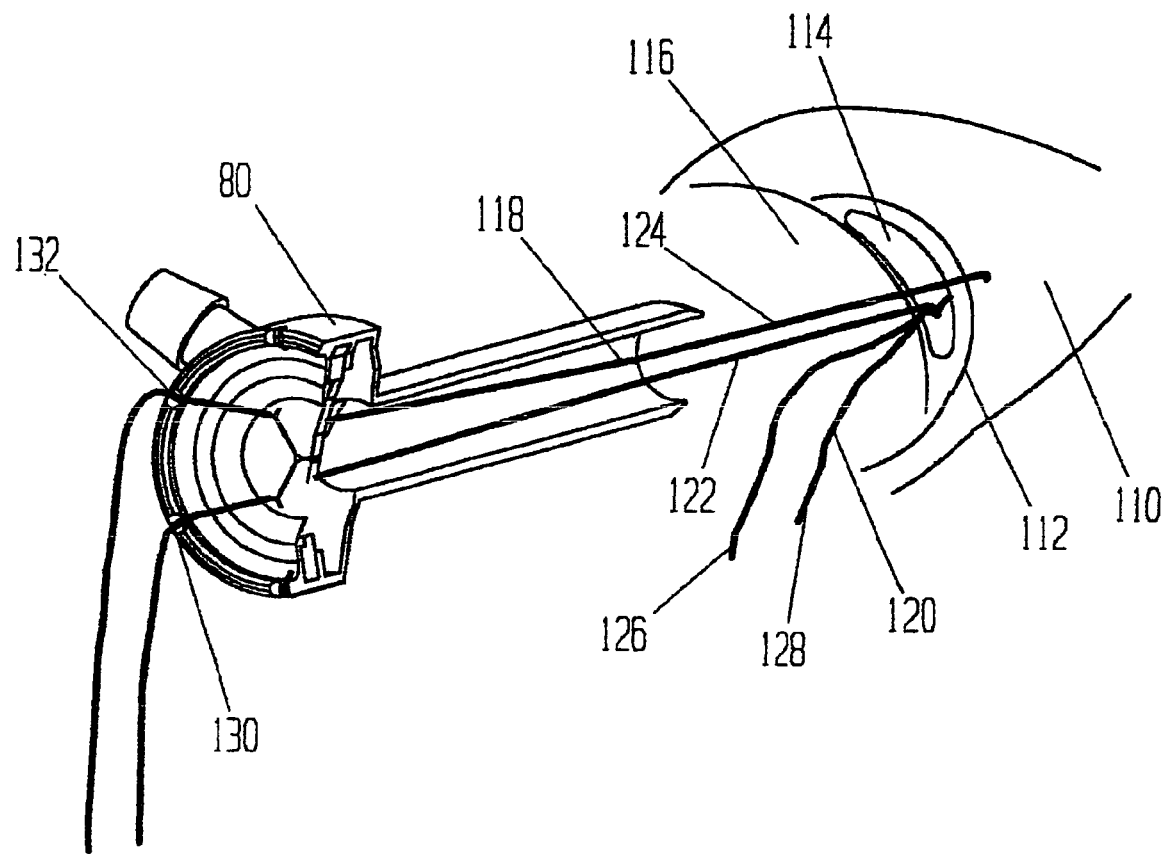
FIG. 18 is a perspective view of the object of FIG. 14 during use.

Use of the suture isolator during arthroscopic repair of a rotator cuff tear is shown in FIG. 18. Use is illustrated using the embodiment of FIG. 17, cannula 80 having integral suture retaining slots. Use of the other embodiments, each with the associated cannula, is identical to that illustrated. Cannula 80 is positioned in a portal so as to function as the working cannula, used for passing instruments and sutures. Rotator cuff 110 has a tear 112. Trough 114 has been created in humeral head 116 and an anchor such as the Arthex Corkscrew Suture Anchor™ loaded with two sutures 118 and 120 is inserted into humeral head 116 in trough 114. Sutures 118 and 120 slide freely in the eyelet of the anchor and are differently colored to allow easy identification of the leg pair of a given suture. Suture legs 122 and 124 form a pair, and legs 126 and 128 form another pair.

In FIG. 18, leg 122 has been retrieved through cannula 80 and removably secured in slot 130, slight tension being maintained in leg 122. Using a suture passing instrument such as the Arthex Needle Punch™, leg 124 has been passed through cuff 110, retrieved through cannula 80, and removably secured in slot 132 with slight tension being maintained in leg 124. Insertion of the instrument, passing of the suture, and retrieval of the leg are accomplished without interference from leg 122 because leg 122 is colinear with the cannula and the instrument motions, and slight tension is maintained in leg 122. Subsequently, legs 126 and 128 will be retrieved in the same manner as legs 122 and 124. Suture 118 is then used as a traction suture. The tension in legs 122 and 124 is increased so as to move the edge of cuff 110 to the insertion point. The cuff is then secured in place using suture 120 by sliding knots in the usual manner. Tangling during knot tying is prevented by separation of the sutures and slight tension maintained in the sutures by the suture isolator cannula. Suture 118 is then tied in the same manner as suture 120.

FIGS. 23, 24 and 25 represent a diagrammatic sequence showing how the invention can be used to organize sutures and apply tension to the rotator cuff edge to accomplish reduction of the rotator cuff edge to its insertion area when doing a multi-anchor repair. FIG. 23 demonstrates a top view of the rotator cuff edge 160, the cuff insertion area 161 and the anticipated anchor insertion points 170 and 171. FIG. 24 shows anchors 172 and 173 deployed. Sutures 175, 176, 177 and 178 have been passed through the rotator cuff and diagrammatically secured by the invention represented by the solid line 180. FIG. 25 shows the rotator cuff edge reduced into its' insertion area by tensioning sutures 175, 176, 177 and 178. Each suture pair is locked into the invention 180, holding tension on each suture pair, spreading the reduction force over multiple points. In addition, the patient's arm can be abducted during this maneuver to bring the insertion area closer to the rotator cuff edge. The suture pairs can then be tied down and cut, one pair at a time. The untied suture pairs hold the rotator cuff edge reduced, facilitating the knot tying process.

Figure 19:
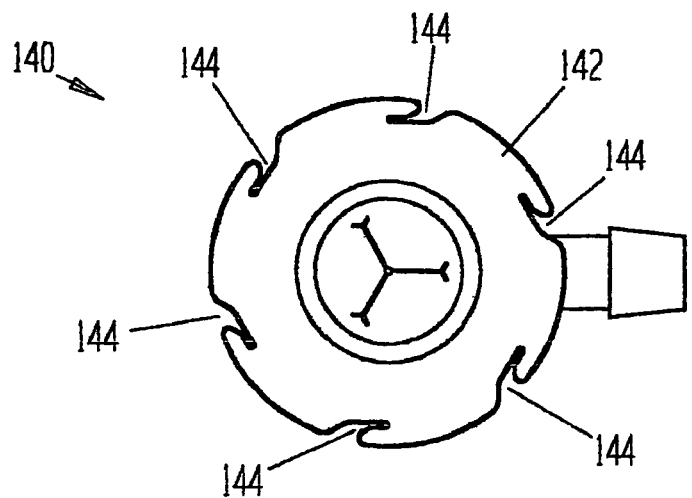
FIG. 19 is a proximal axial view of an alternate embodiment.
Figure 20:
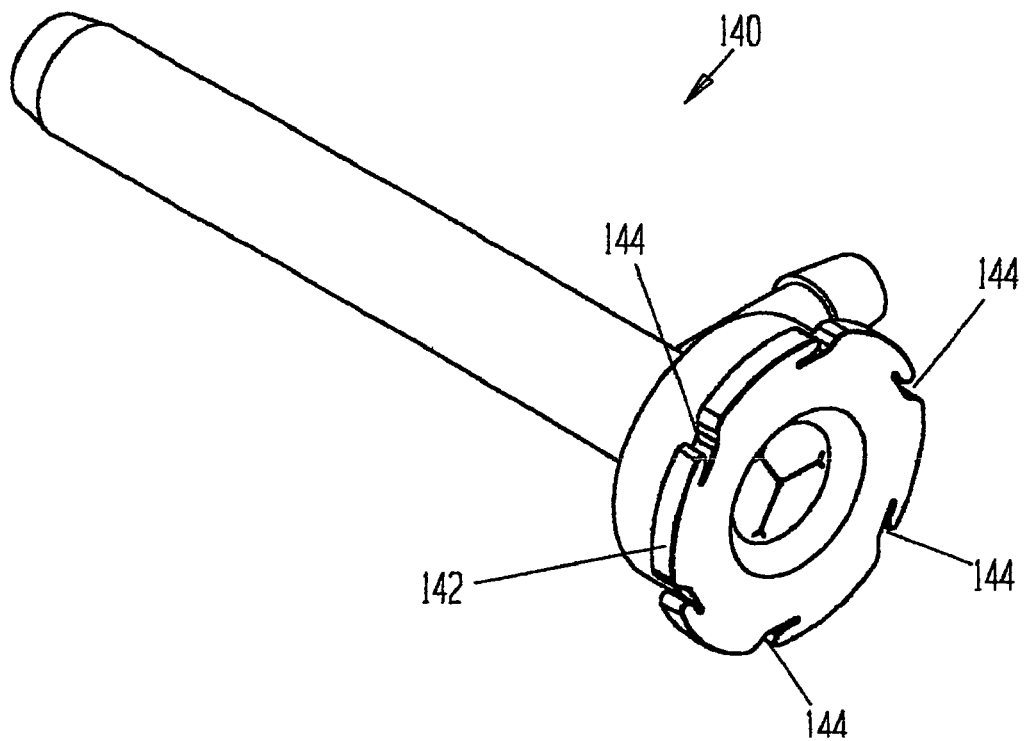
FIG. 20 is a perspective view of the object of FIG. 19.
Figure 21:
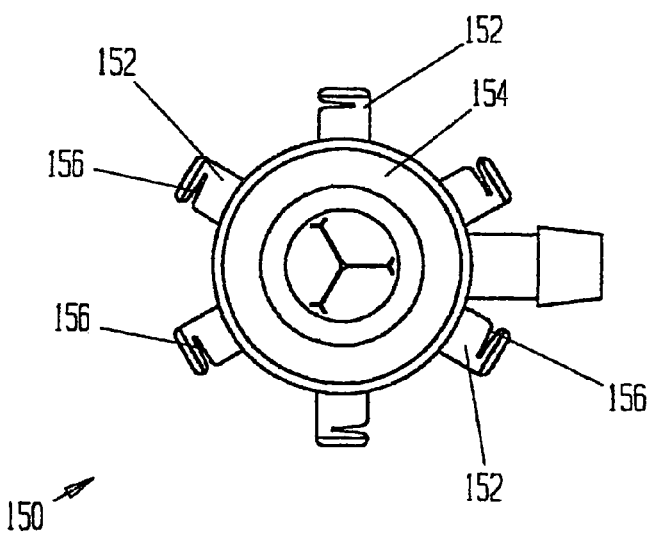
FIG. 21 is a proximal axial view of an alternate embodiment.
Figure 22:
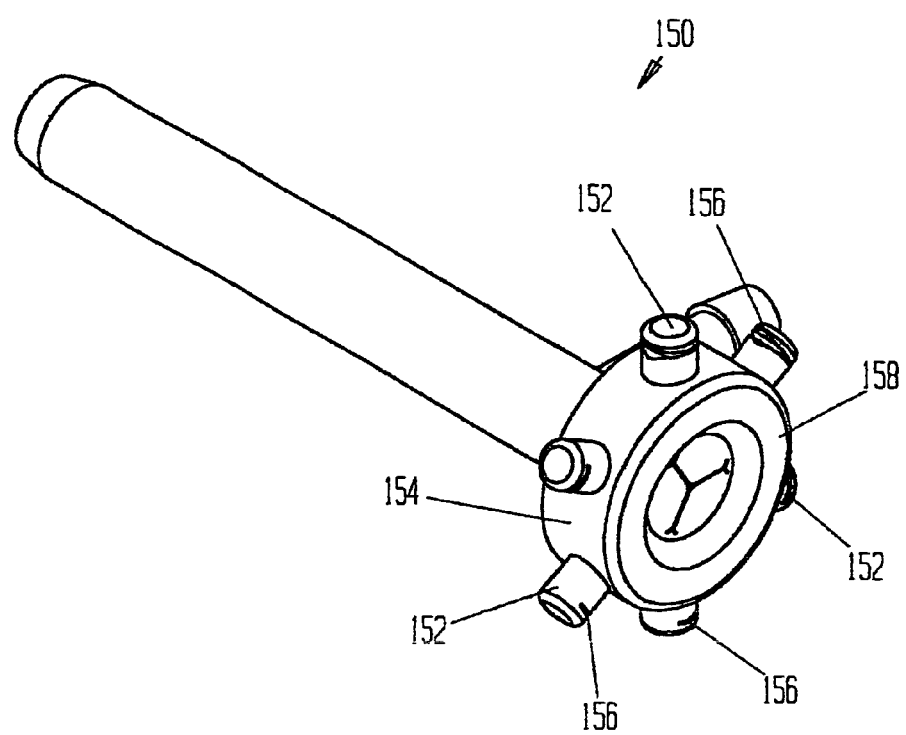
FIG. 22 is a perspective view of the object of FIG. 21.

Other configurations are possible in which the positions of the suture retaining slots are varied. For instance FIGS. 19 and 20 show a cannula 140 in which a circumferential rim 142 is added to the proximal end of the cannula and a plurality of circumferential slots 144 are formed in the rim. In another embodiment, cannula 150, shown in FIGS. 21 and 22, a plurality of cylindrical protrusions 152 are formed on the circumferential surface 158 of the cannula proximal portion 154, with slots 156 formed in the protrusions. In this embodiment suture retrieved through the cannula is positioned in the slots in the seal as in cannula 80 (FIGS. 14 through 18), is wrapped around a protrusion 152 and positioned in slot 154. Those of skill in the art will recognize that in all cases where a suture organizer is shown integral to a cannula, it may alternatively be removably secured thereto, and vice versa.

When the suture isolator of FIGS. 1 through 3 is used with the cannula of FIGS. 4 through 6 as shown in FIGS. 7 through 9, fluid may spray in an uncontrolled fashion through seal 54 when a suture is tensioned. This spray is a nuisance, as it may soak items in the area including the surgeon. In an alternate embodiment of the invention herein described, a deformable spray shield prevents uncontrolled spraying of fluid which leaks past the cannula seal. Referring to FIGS. 26 through 29, suture isolator 201 has a proximal end 202, a distal end 204, outer diameter 206 and length 208. Distal portion 210 has a recess 212 formed therein, recess 212 having a cylindrical portion 214 of diameter 216 and a tapered portion 217 in which the diameter increases to diameter 218. Proximal portion 220 has a cylindrical recess 222 of diameter 224 formed therein so as to produce proximal rim 226. Proximal rim 226 has a plurality of slots 228 of depth 230 having a distal portion 232 of width 234 and a tapered proximal portion 236. Width 234 of distal portion 232 is less than the thickness of the suture generally used for arthroscopic rotator cuff repair so that suture removably placed in slots 228 is held securely.

Figure 26:
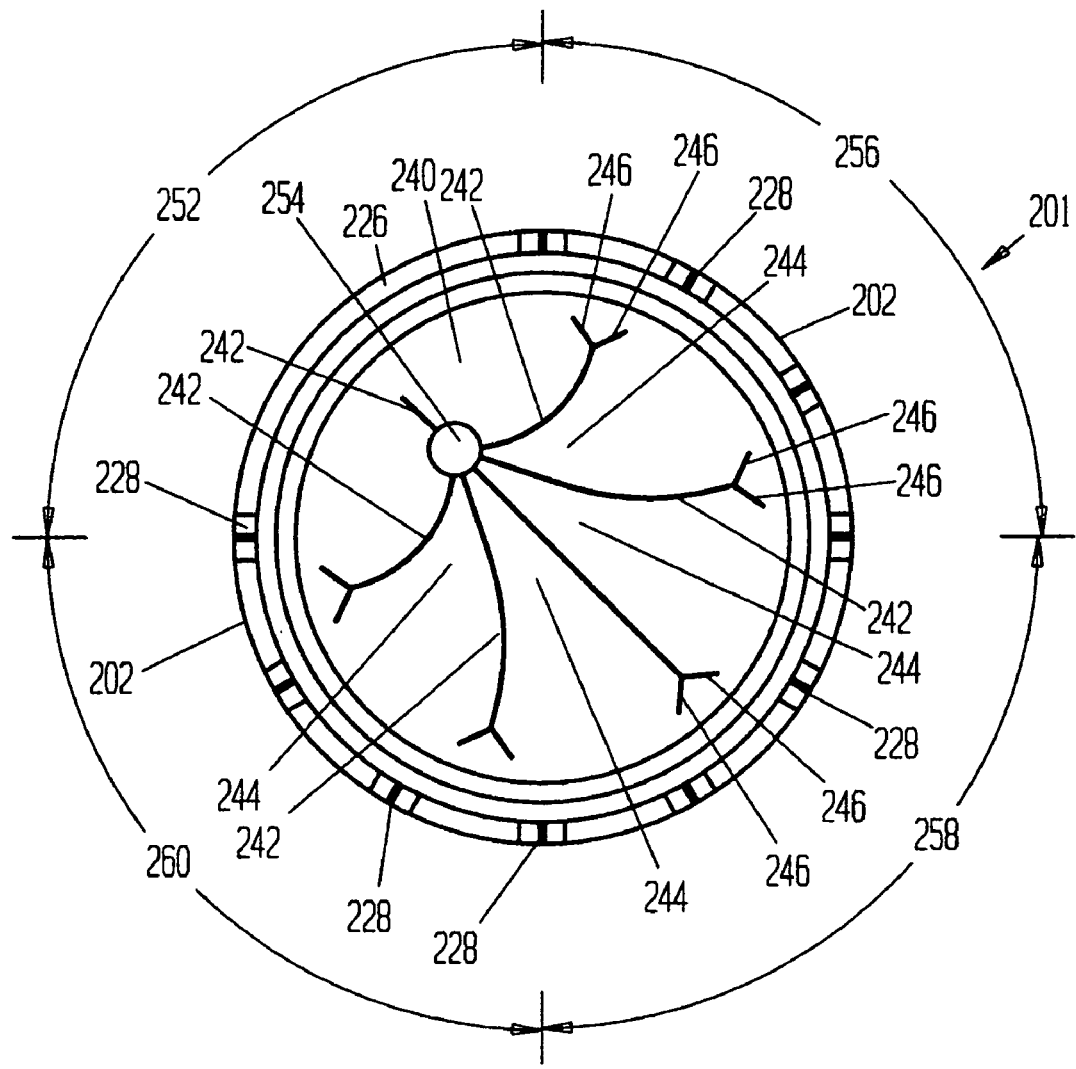
FIG. 26 is a distal axial view of an alternate embodiment.
Figure 27:
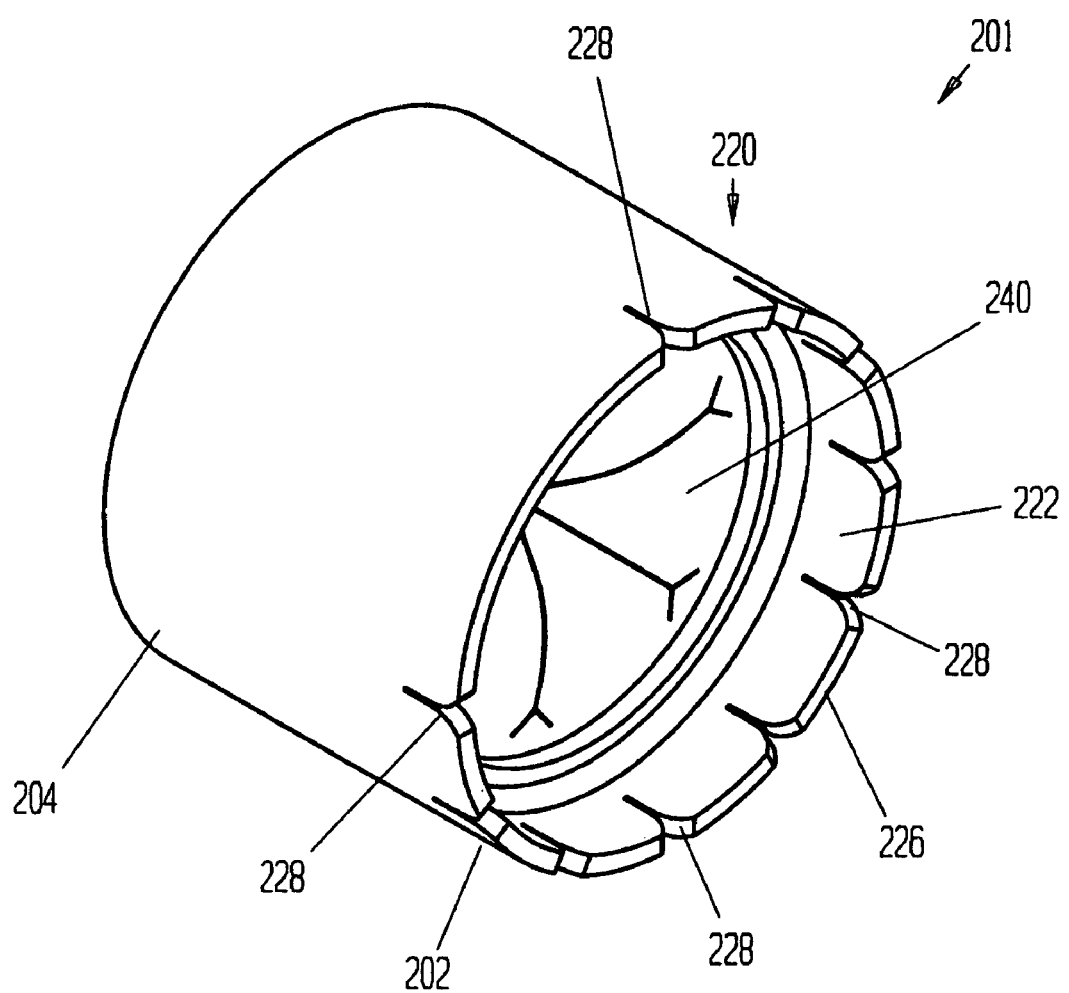
FIG. 27 is a perspective view of the objects of FIG. 26.
Figure 28:
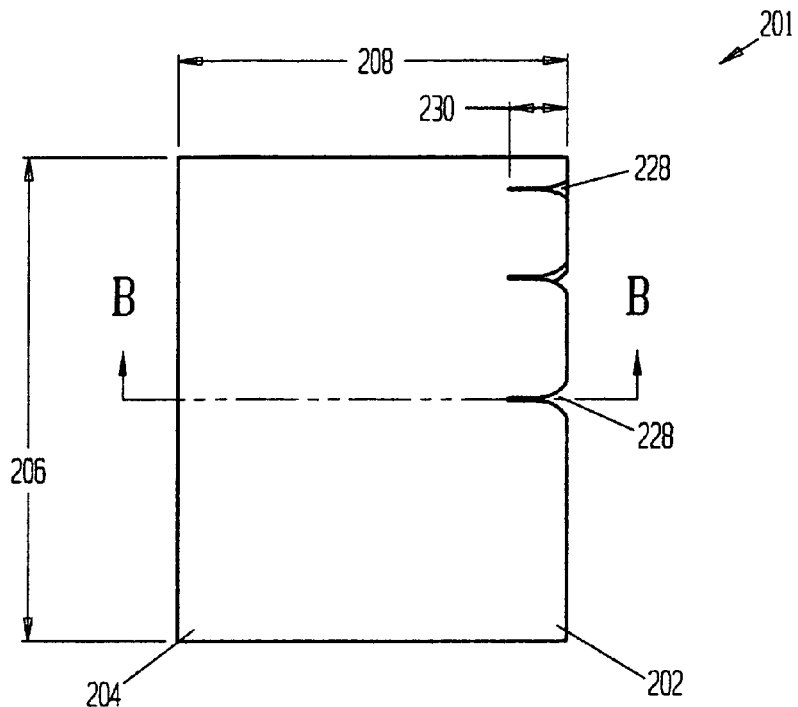
FIG. 28 is a top view of the objects of FIG. 26.

Isolator 201 is made of a rigid metallic or polymeric material. Spray shield 240, made from a suitable elastomeric material, has a plurality of slits 242 forming a plurality of flaps 244, slits 242 terminating in angled slits 246. Ring 250 retains splash guard 240 in cylindrical portion 214 of recess 212. When viewed axially as in FIG. 26, isolator 201 has an instrument-passing area 252 with opening 254 in spray shield 240, and suture-parking areas 256, 258 and 260 comprising slits 242, angled slits 246 and slots 228. In the preferred embodiment four areas are provided in separate quadrants, though other geometries are possible so long as opening 254 is off center. Also, as with other embodiment described herein, The distal portion of the isolator may be an add-on piece or integrally formed.

Figure 29:
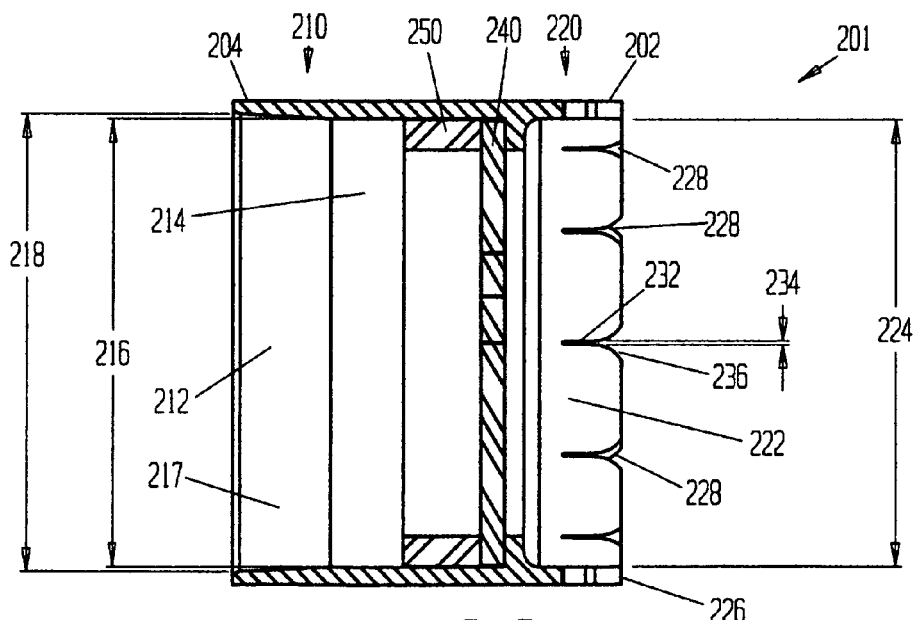
FIG. 29 is a side elevational sectional view of the objects of FIG. 26 at location A-A.
Figure 30:
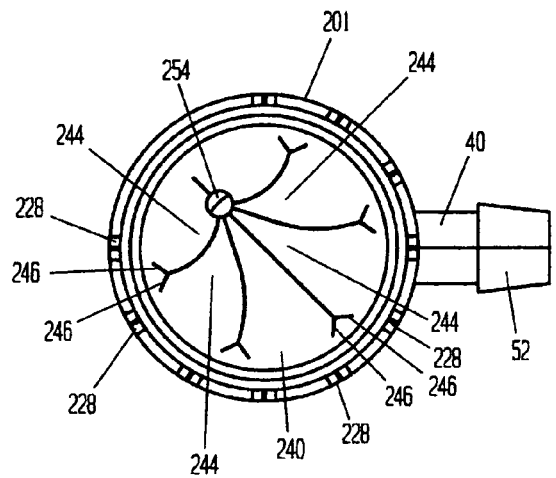
FIG. 30 is a distal axial view of the embodiment of FIG. 26 mounted to a cannula.
Figure 31:
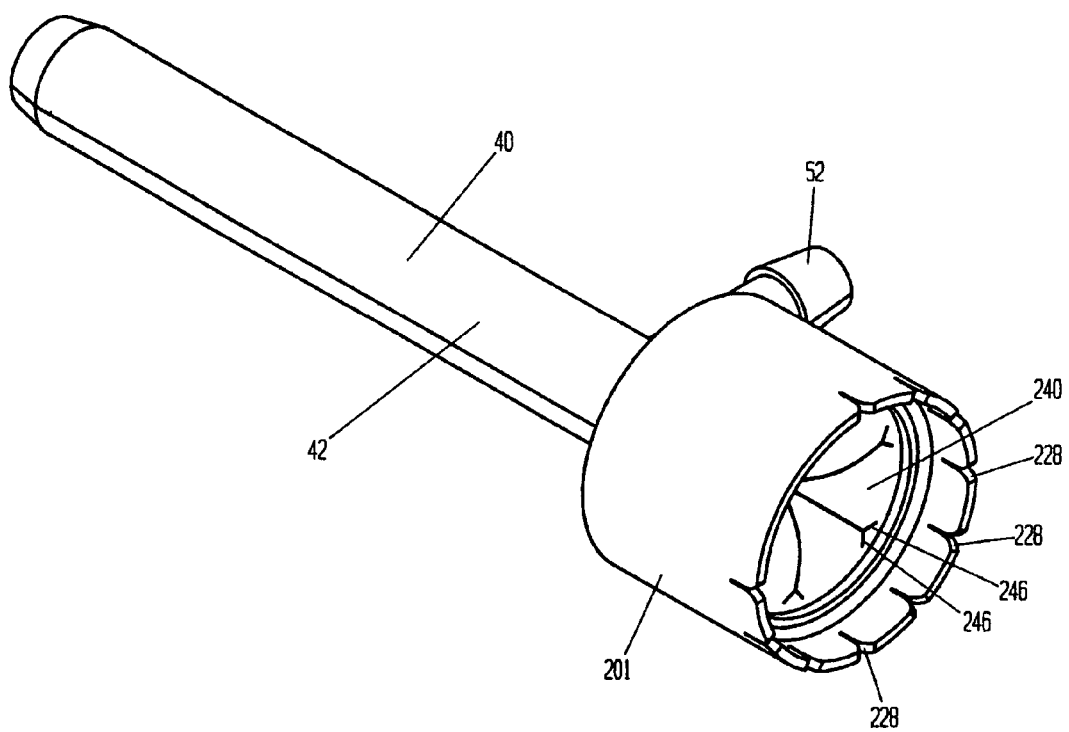
FIG. 31 is a perspective view of the objects of FIG. 30.
Figure 32:
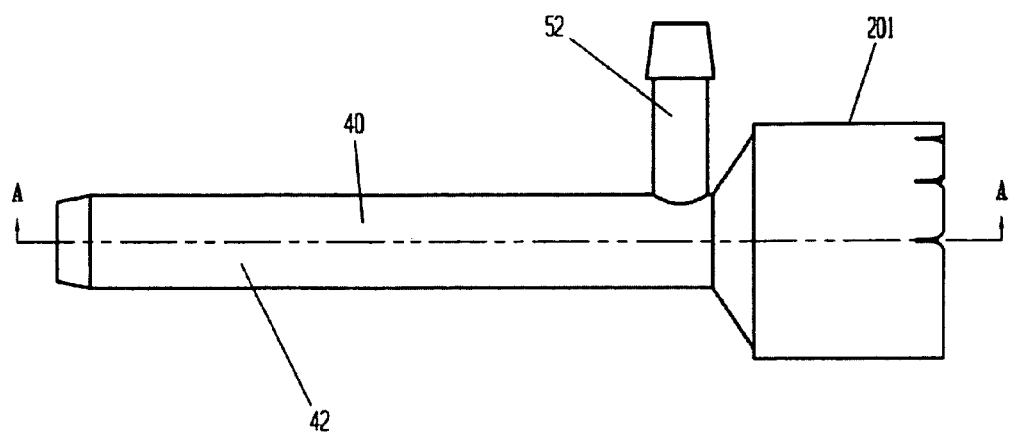
FIG. 32 is a top view of the objects of FIG. 30.
Figure 33:
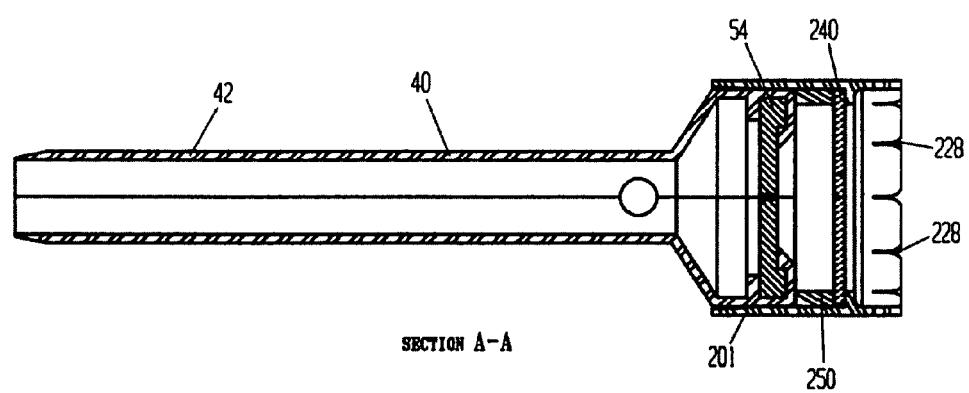
FIG. 33 is a side elevational sectional view of the objects of FIG. 30.

Referring now to FIGS. 30 through 33 showing suture isolator 201 removably mounted to the proximal end of cannula 40 (FIGS. 4 through 6), proximal portion 46 of cannula 40 is slightly greater than diameter 216 of cylindrical portion 214 of distal recess 212 of suture isolator 201, and slightly less than diameter 218 of tapered portion 217 of recess 212 (FIG. 29). Suture isolator 201 is removably mounted to cannula 40 as shown in the figures, proximal portion 46 of cannula 40 contacting and nesting against ring 250 of isolator 201. Spray shield 240 of isolator 201 is positioned proximal to seal 54 of cannula 40.

Figure 34:
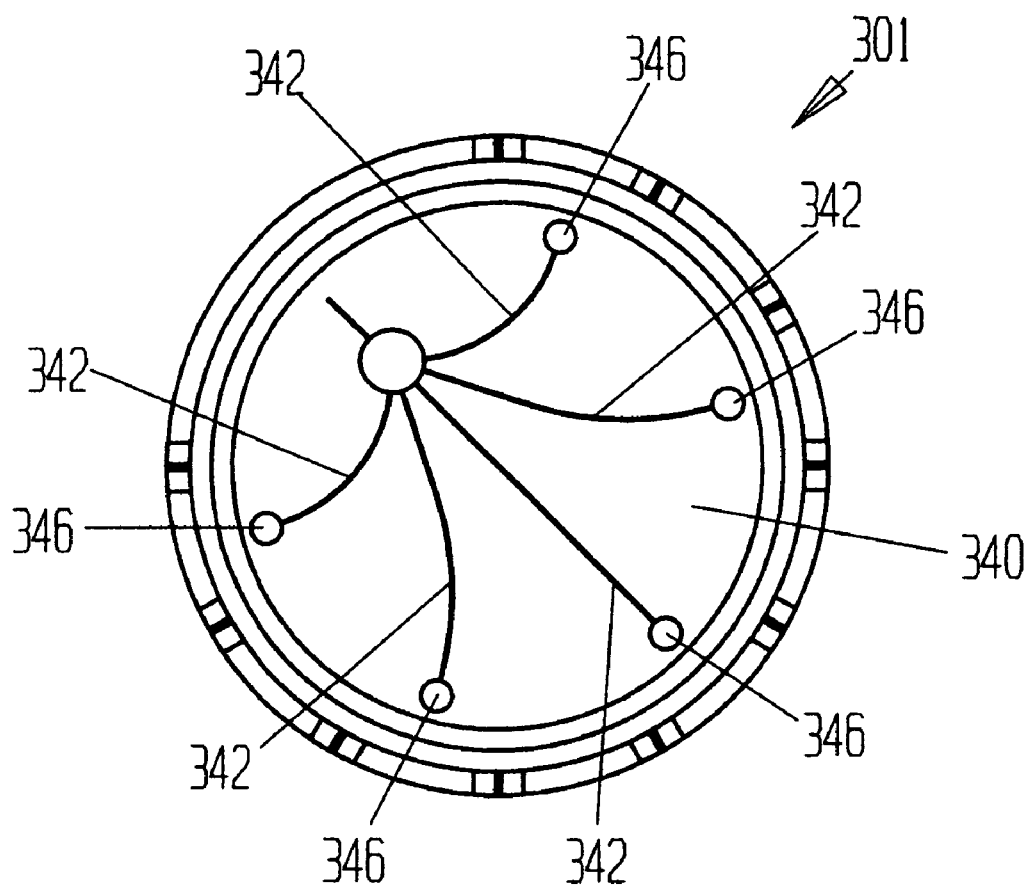
FIG. 34 is a distal axial view of an alternate embodiment similar to the embodiment of FIGS. 26 to 34 but with a modified splash guard.

During use instruments are passed through isolator 201 and cannula 40 using opening 254 in area 252 of isolator 201, spray shield 240 deforming as required to allow easy passage of the instruments. Sutures which have been retrieved are positioned in angled slits 246 and slots 228 so as to maintain slight tension on the sutures. When the sutures have been secured in slots 228, flaps 244 return to and maintain their closed positions so as to prevent uncontrolled spraying of liquid leaking past seal 54 of cannula 40. In an alternate embodiment shown in FIG. 34, suture isolator 301 with spray shield 340 has openings 346 for suture passage at the ends of slits 342, rather than the angled slits 246 of isolator 201 (FIGS. 26 through 29). Such a configuration is also possible with the other embodiments described herein, including, for example, isolator 80 shown in FIG. 17.

We claim:

1. A suture organizer comprising a tubular body having a proximal end, a distal end, and a cylindrical wall extending therebetween that surrounds and encloses a central bore that defines a longitudinal central axis, wherein:

the distal end of the tubular body is provided with a cylindrical recess that fixedly engages the proximal end of a cannula having at least one inflow lumen for supplying an irrigant; and the proximal end of the tubular body is provided with a rigid peripheral rim, said rigid peripheral rim having a plurality of suture retaining features disposed about an outer edge thereof for receiving, organizing and tensioning sutures during rotator cuff repair or other arthroscopic procedures; and the tubular body further includes a spray shield disposed within said central bore that minimizes fluid flow therethrough, said spray shield comprising a deformable elastomeric seal having formed therein at least one eccentric opening for instrument passage, said opening positioned off-center relative to the central axis of the bore to minimize outward spraying of fluid during use, and a plurality of radial slits extending outwardly from said eccentric instrument passage opening toward said tubular body cylindrical wall.

2. The suture organizer of claim 1, wherein one or more of said radial slits is provided with an angled terminus through which a suture may pass.

3. The suture organizer of claim 1, wherein one or more of said radial slits is provided with a circular opening through which a suture may pass.

4. The suture organizer of claim 1, wherein said radial slits have a length ranging from 0.5 mm to 2 mm.

5. The suture organizer of claim 1, wherein said cylindrical recess mates with a cylindrical proximal portion of said cannula.

6. The suture organizer of claim 1, wherein said rigid peripheral rim is made of a rigid metallic or polymeric material.

7. The suture organizer of claim 5, wherein said rigid peripheral rim extends proximally away from the tubular body, further wherein said plurality of suture retaining features comprise a series of slots formed in an external surface of said peripheral rim.

8. The suture organizer of claim 6, wherein said slots include a proximal opening that defines a central axis that is parallel to the central bore axis.

9. The suture organizer of claim 6, wherein said slots comprise a wide proximal opening that tapers to a narrow suture-securing distal portion.

10. The suture organizer of claim 1, wherein said rigid peripheral rim comprises a circumferential surface extending outwardly away from the body in a direction that is normal to the central bore axis, further wherein said plurality of suture retaining features comprise a series of slots formed in said circumferential surface.

11. The suture organizer of claim 1, wherein said plurality of suture retaining features comprise a series of protrusions provided on an external surface of said peripheral rim around which a suture material may be wound, said protrusions extending outwardly away from the body in a direction that is normal to the central bore axis.

12. The suture organizer of claim 10, wherein said protrusions further comprise cylinders having suture-securing slots provided thereon.

13. The suture organizing system of claim 12, wherein the suture organizer is integral with said cannula.

14. The suture organizing system of claim 12, wherein the suture organizer is removably secured to said cannula.

15. A suture organizing system comprising:
   a. a cannula having at least one inflow lumen for carrying irrigant, said central lumen defining a central axis; and
   b. a suture organizer as defined in claim 1, wherein said suture organizer is coupled to the proximal end of said cannula such that the central axis of the cannula is aligned with the central axis of the central bore.

16. A method for reducing a tear in rotator cuff during arthroscopic surgery, comprising the steps of:
   i. providing the suture organizing system of claim 12;
   ii. placing an anchor having a set of sutures into a humeral head, with one of the sutures being passed around a portion of the tear;
   iii. retrieving the set of sutures through the cannula;
   iv. parking and tensioning the retrieved sutures in the suture retaining features of the suture organizer to avoid entanglement;
   v. repeating steps iii) and iv) as necessary; and
   vi. securing the cuff in place using sliding knots on the various sets of sutures.

17. The method of claim 16, wherein the sets of sutures are color-coded.

* * * * *